United States Patent [19]

Tranberg

[11] Patent Number: 4,622,908

[45] Date of Patent: Nov. 18, 1986

[54] METHOD OF MANUFACTURING SLEEVE SHAPED BODY PROTECTORS

[75] Inventor: Per Tranberg, Lerum, Sweden

[73] Assignee: Volcano International Medical AB, Sweden

[21] Appl. No.: 663,191

[22] Filed: Oct. 22, 1984

[30] Foreign Application Priority Data

Dec. 1, 1983 [AU] Australia ............................ 21867/83

[51] Int. Cl.[4] ......................... D05B 1/08; A41D 27/24
[52] U.S. Cl. .................................. 112/262.2; 112/418; 112/441; 2/275; 128/80 C
[58] Field of Search ..................... 112/262.2, 418, 419, 112/441, 163, 414, 164; 2/2.1 R, 24, 275; 128/80 C, 165, 77; 138/128

[56] References Cited

U.S. PATENT DOCUMENTS

| | | | |
|---|---|---|---|
| 3,115,879 | 12/1963 | Kaplan | 128/165 X |
| 3,744,052 | 7/1973 | Rector | 2/2.1 R X |
| 4,084,586 | 4/1978 | Hettick | 128/80 C |

FOREIGN PATENT DOCUMENTS 2336833 2/1974 Fed. Rep. of Germany ...... 112/418

*Primary Examiner*—Werner H. Schroeder
*Assistant Examiner*—Andrew M. Falik
*Attorney, Agent, or Firm*—Wegner & Bretschneider

[57] ABSTRACT

A sleeve shaped protector for a portion of a limb is manufactured from a sheet of cloth comprising a core of resilient, porous material laminated upon both faces with a sparse fabric. The sheet is cut to suitable size and rolled into a tubular member, whereupon a strip of fabric, being substantially non-resilient in its transverse direction is laid to cover the joint between the meeting edges of the sheet. The strip and the sheet are then sewn together using a machine having at least two needles to each side of the joint, the machine further having means for criss-crossing the threads from the needle to opposite sides of the joint, across the latter, at the face of the cloth remote from the strip.

2 Claims, 3 Drawing Figures

METHOD OF MANUFACTURING SLEEVE SHAPED BODY PROTECTORS

BACKGROUND OF THE INVENTION

The present invention refers to sleeve-shaped protectors for portions of the human body, but also useful for certain animals, such as horses. In use such protectors will support an injured limb, for instance a knee or an elbow, while simultaneously holding it warm so that circulation of blood is increased.

These protectors are made of cloth comprising a core of resilient material about 5 mm thick, laminated upon both sides with a coarse fabric. The core is usually made of a chemically expanded compound so it will become heat insulating without any marked capacity for accumulating moisture (sweat).

A sheet of cloth is cut to a size suited to cover the actual portion of the limb, and may be provided with means, such as bur fasteners or ribbons, so it can be applied as a bandage, but may also be formed into a tubular member. In the latter case the meeting edges of the cloth are glued or vulcanized together, the joint being sometimes reinforced by sewing.

SUMMARY OF THE INVENTION

In order to facilitate production it is now proposed, that the edges of the cloth are sewn together without any glueing. This will require special attention to the sewing operation.

A method according to the invention of manufacturing body protectors comprises the steps of locating a strip of fabric being substantially non-resilient in its transverse direction along the joint between the meeting edges of the sheet, and sewing this strip to the sheet using a machine having at least two needles to each side of the joint, the machine further having means for criss-crossing the threads from the needles to opposite sides of the joint, across the latter at the face of the cloth remote from the strip.

DETAILED DESCRIPTION

Figure 1:
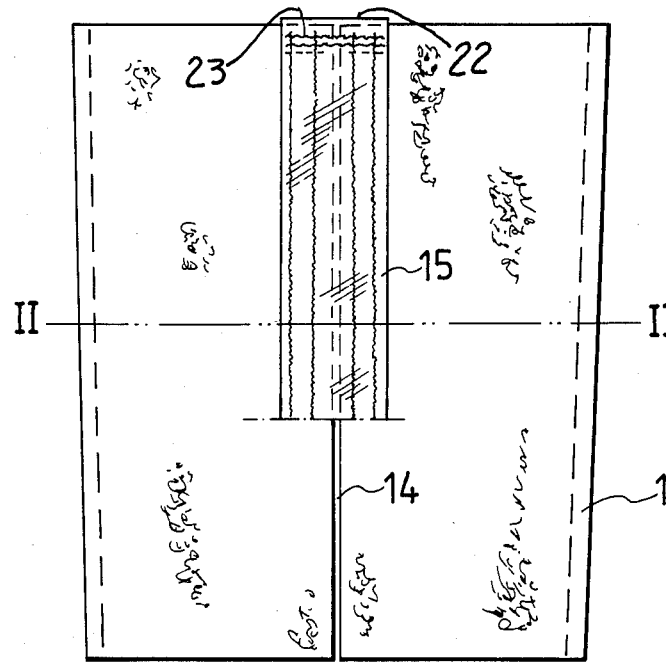
FIG. 1 shows a plan view of a protector according to the invention.

The cloth used comprises a core 10 of cellular foam rubber material, preferably NEOPRENE, about 5 mm thick. Such material will have the necessary rigidity to form an elastic support, it will be heat insulating, and it will not markedly absorb moisture.

The core material is on both faces laminated with a woven fabric 11, 12, of some synthetic yarn, for instance of nylon, which has about the same elasticity as the mateterial in the core 10. It should furthermore be of a coarse or open weave, to permit the passage of moisture. At least the inward layer of fabric should be of a nature facilitating the mounting and the wearing of the protector upon the limb.

A sheet of cloth is cut to suitable size, and is formed to a tubular member 13, in which juxtaposed edges of the sheet run parallel along a joint 14. This has to be satisfactorily closed so the protector sleeve can be pulled on and off, and will retain the shape of the sleeve in use.

A strip 15 of fabric which is substantially non-resilient in the transverse direction of the strip is placed over the joint 14, preferably at the outside face of the sleeve, and is sewn to the cloth by means of a machine having at least two needles 16, 17 and 18, 19 to each side of the gap between the edges of the sheet.

Figure 2:
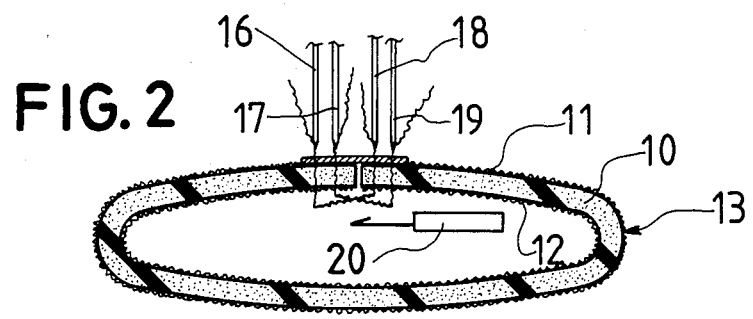
FIG. 2 shows a section therethrough, along line II—II in FIG. 1, and during the sewing operation.
Figure 3:
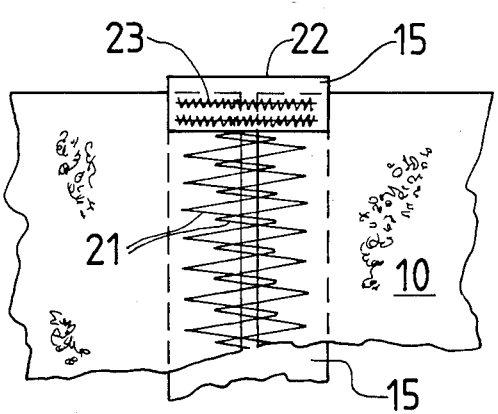
FIG. 3 shows, on a slightly larger scale, the reverse side of a portion of the joint.

This is schematically illustrated in FIG. 2. The machine furthermore has means (very schematically indicated at 20) for knitting the yarns forced through the cloth by the needles 16–19 in a criss-cross pattern 21 across the gap between the edges of the sheet. Four seams are thus produced, two on each side of the joint 14, which are shown in FIG. 1 at 23-26.

The seams thus obtained will bind the edges together at the inside of the sleeve in a manner which does not differ much from the surrounding fabric, and will thus be agreeable to the bearer of the protector. The four seams joined at the inside of the sleeve will, together with the strip, efficiently hold the edges together.

The parts of the protector subjected to most strain are the portions at the ends of joint 14. The strip 15 is therefore selected somewhat longer than the height of the protector, and the ends 22 of the strip are folded down over the ends of the joint, and are sewn with transverse seams 23 to securely close the ends of the joint.

What I claim is:

1. A method of manufacturing sleeve-shaped protectors for portions of the body and made of a sheet of cloth comprising a core of resilient, porous material laminated upon both faces with a coarse fabric, the sheet being cut to suitable size and rolled into a tubular member to thereby form a joint between the two meeting edges, comprising the steps of:

locating a strip of fabric which is substantially non-resilient in its transverse direction along the joint between the meeting edges of the sheet, and sewing said strip to the sheet using a machine having at least two needles to each side of the joint, operating the machine for criss-crossing the threads from the needles to opposite sides of the joint, across the latter, at the face of the cloth remote from the strip.

2. The method as claimed in claim 1, wherein said strip of fabric extends past both ends of said sheet, said method further comprising the steps of:

doubling over the portion of said fabric extending past each end of said sheet, and sewing at least one seam at each end of said sheet transversely across said joint.

* * * * *